United States Patent
Ding et al.

(10) Patent No.: US 11,928,948 B2
(45) Date of Patent: Mar. 12, 2024

(54) ENVIRONMENTAL DATA MONITORING METHOD AND MONITORING SYSTEM

(71) Applicant: CHANGXIN MEMORY TECHNOLOGIES, INC., Hefei (CN)

(72) Inventors: Yunxiao Ding, Hefei (CN); Xiaohui Liu, Hefei (CN)

(73) Assignee: CHANGXIN MEMORY TECHNOLOGIES, INC., Hefei (CN)

( * ) Notice: Subject to any disclaimer, the term of this patent is extended or adjusted under 35 U.S.C. 154(b) by 22 days.

(21) Appl. No.: 17/579,837

(22) Filed: Jan. 20, 2022

(65) Prior Publication Data

US 2022/0148407 A1 May 12, 2022

Related U.S. Application Data

(63) Continuation of application No. PCT/CN2021/104814, filed on Jul. 6, 2021.

(30) Foreign Application Priority Data

Oct. 19, 2020 (CN) .......................... 202011119320.0

(51) Int. Cl.
*G08B 21/12* (2006.01)
*G01N 33/00* (2006.01)
*H01L 21/66* (2006.01)

(52) U.S. Cl.
CPC .......... *G08B 21/12* (2013.01); *G01N 33/0006* (2013.01); *G01N 33/0063* (2013.01); *G01N 33/007* (2013.01); *H01L 22/26* (2013.01)

(58) Field of Classification Search
CPC .............................. G08B 21/12; G01N 33/0063
See application file for complete search history.

(56) References Cited

U.S. PATENT DOCUMENTS

2003/0154055 A1  8/2003  Yoshimura
2020/0044787 A1  2/2020  Wang et al.

FOREIGN PATENT DOCUMENTS

| CN | 102111428 A | | 6/2011 | |
|---|---|---|---|---|
| CN | 109068147 | * | 9/2018 | ......... H04N 21/2347 |
| CN | 109194755 | * | 9/2018 | ............. H04L 67/10 |
| CN | 109489171 | * | 11/2018 | ............. F24F 11/58 |
| CN | 109026157 A | | 12/2018 | |
| CN | 109348446 A | | 2/2019 | |
| CN | 110851290 | * | 11/2019 | ............. G06F 16/27 |
| CN | 110569179 A | | 12/2019 | |
| CN | 110610295 A | | 12/2019 | |
| CN | 110855402 A | | 2/2020 | |
| CN | 111082896 A | | 4/2020 | |
| KR | 101672724 | * | 5/2015 | ........... G06F 17/303 |

* cited by examiner

*Primary Examiner* — Hongmin Fan
(74) *Attorney, Agent, or Firm* — Cooper Legal Group, LLC

(57) ABSTRACT

A method for monitoring environmental data and a monitoring system are provided. The method includes that: a second server receives first environmental data from a first server; the second server determines that data loss occurs in the first environmental data; the second server obtains lost data in the first environmental data from the first server; the second server obtains second environmental data according to the first environmental data and the lost data; and responsive to a concentration of a sampled gas in the second environmental data exceeding a preset concentration threshold, the second server sends warning information to a terminal device.

14 Claims, 11 Drawing Sheets

ENVIRONMENTAL DATA MONITORING METHOD AND MONITORING SYSTEM

CROSS-REFERENCE TO RELATED APPLICATION

This application is a continuation application of International Patent Application No. PCT/CN2021/104814, filed on Jul. 6, 2021, which claims priority to Chinese Patent Application No. 202011119320.0 filed to the China National Intellectual Property Administration on Oct. 19, 2020 and entitled "ENVIRONMENTAL DATA MONITORING METHOD AND MONITORING SYSTEM". International Patent Application No. PCT/CN2021/104814 and Chinese Patent Application No. 202011119320.0 are incorporated herein by reference in their entireties.

BACKGROUND

With the increase in the complexity of the preparation process of semiconductor products and the continuous reduction of feature sizes of semiconductor products, the impact of air pollutants on products has become a key issue that needs to be paid attention to in the preparation process of semiconductor products. For example, ammonia and acid gases generated in the ambient air may affect the formation of metal wires, and the reaction of ammonia and acid gases may generate salts that affect the yield of semiconductor products. Therefore, it is necessary to prepare semiconductor products in a clean room and monitor airborne molecular contaminants in the clean room environment.

In the existing technology, during monitoring of the airborne molecular contaminants in the clean room, concentration data of airborne molecules in the clean room is collected by a measurement device, the collected concentration data is sent to a monitoring system, and the monitoring system determines whether the concentrations of different airborne molecules exceed preset concentrations, and if yes, an alarm is issued to notify a staff to deal with the airborne molecular contaminants in the clean room.

However, in the existing technology, during monitoring of the airborne molecular contaminants in the clean room, it is easy to lose concentration data during data transmission, which in turn causes the problem of inaccurate monitoring results of airborne molecular contaminants in the clean room.

SUMMARY

This disclosure relates to the semiconductor preparation environmental monitoring technology, and in particular, to a method for monitoring environmental data and a monitoring system.

This disclosure provides a method for monitoring environmental data and a monitoring system. By determining whether data loss occurs in data transmission, if data loss occurs, then the lost data is re-obtained, to obtain complete data (that is, there is no lost data), and whether the gas concentration exceeds a concentration threshold is determined according to the complete data, and warning information is generated for a gas that exceeds the concentration threshold.

This disclosure provides a method for monitoring environmental data, applied to a monitoring system including a first server and a second server, and the method includes the following operations:

the second server receives first environmental data from the first server;

the second server determines that data loss occurs in the first environmental data;

the second server obtains lost data in the first environmental data from the first server;

the second server obtains second environmental data according to the first environmental data and the lost data; and responsive to a concentration of a sampled gas in the second environmental data exceeding a preset concentration threshold, the second server sends warning information to a terminal device.

According to the method for monitoring environmental data provided in this disclosure, in a case that the second server determines that data loss occurs in the first environmental data, the lost data is obtained from the first server. The second server obtains the second environmental data according to the first environmental data and the lost data, and determines, according to the second environmental data, whether to send warning information to a terminal device. The second server determines whether a concentration of a sampled gas in a clean room exceeds a preset concentration threshold based on complete data of the concentrations of the sampled gases in the clean room.

DETAILED DESCRIPTION

Figure 1:
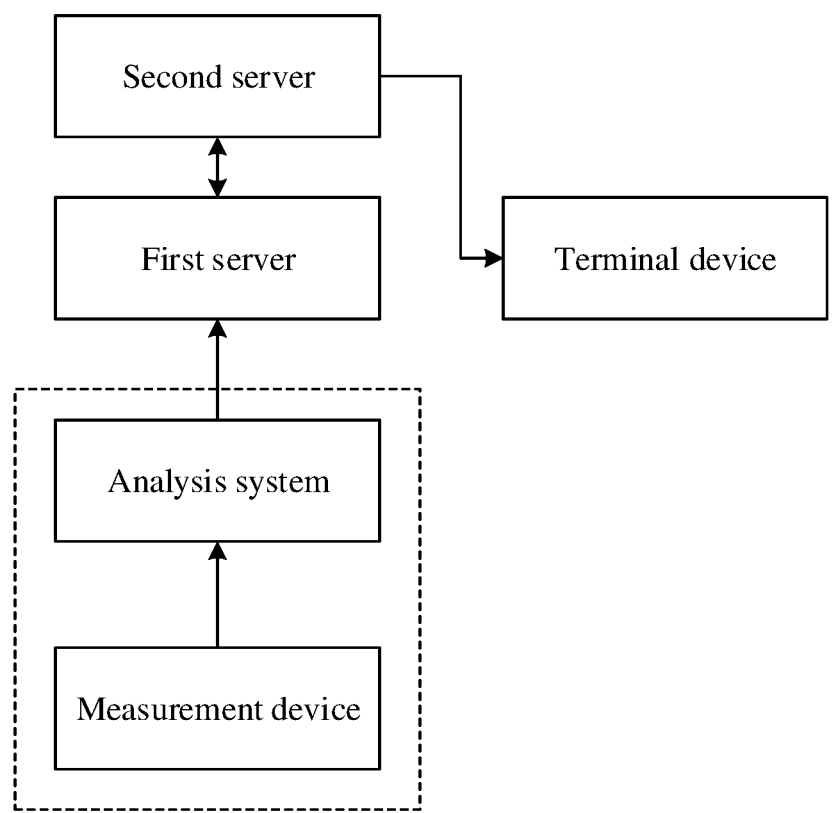
FIG. 1 is a schematic diagram of an application scenario of a method for monitoring environmental data provided by this disclosure.

The exemplary embodiments are described in detail here, and examples thereof are shown in the accompanying drawings. When drawings are involved in the following description, unless otherwise indicated, the same figure in different drawings indicates the same or similar element. The implementations described in the following exemplary embodiments do not represent all implementations consistent with the disclosure. Instead, the implementations are merely examples of apparatuses and methods consistent with some aspects of the disclosure as detailed in the appended claims.

Semiconductor products such as integrated circuits, microwave devices and optoelectronic devices are widely used in daily life. With the increase in the complexity of the preparation process of semiconductor products and the continuous reduction of feature sizes of semiconductor products, the impact of air pollutants on the semiconductor products has become an issue that needs to be paid attention to in the preparation process of semiconductor products. For example, ammonia and acid gases generated in the ambient air may affect the formation of metal wires, and the reaction of ammonia and acid gases may generate salts that affect the yield of semiconductor products. Therefore, it is necessary to prepare semiconductor products in a clean room and monitor airborne molecular contaminants in the clean room environment. In the existing technology, during monitoring of the airborne molecular contaminants in the clean room, concentration data of airborne molecules in the clean room is collected by a measurement device, the collected concentration data is sent to a monitoring system, and the monitoring system determines whether the concentration of different airborne molecules exceeds a preset concentration. The monitoring system is connected to the terminal device. After determining that the concentration of airborne molecules exceeds the preset concentration, the monitoring system can send warning information to the terminal device. After obtaining the warning information through the terminal device, the staff can process the clean room until the terminal device no longer sends warning information. However, in the existing technology, during monitoring of the airborne molecular contaminants in the clean room, it is easy to lose concentration data during data transmission, and the existing technology does not have a data loss check mechanism. If the concentration data with data loss is used for generating warning information, it may cause the problem of inaccurate monitoring results of airborne molecular contaminants in the clean room.

On this basis, this disclosure provides a method for monitoring environmental data and a monitoring system. By determining whether data loss occurs in data transmission, if data loss occurs, then the lost data is re-obtained, to obtain complete data (that is, there is no lost data), and whether the gas concentration exceeds a concentration threshold is determined according to the complete data, and warning information is generated for a gas that exceeds the concentration threshold. Therefore, the monitoring result of airborne molecular contaminants in the clean room can be prevented from being generated in the case of data loss, and the accuracy of the monitoring result of airborne molecular contaminants in the clean room is improved.

Referring to FIG. 1, the method for monitoring environmental data provided in this disclosure is applied to a monitoring system. The monitoring system includes a first server and a second server. The first server is in communication with a measurement device in a clean room. The measurement device includes an analysis system. The analysis system can collect concentrations of gas molecules collected at multiple sampling points in the clean room, and then send the collected concentrations (that is, initial environmental data) of gas molecules at different sampling points to the first server. The first server processes the initial environmental data to generate first environmental data, and sends the first environmental data to the second server. After processing the first environmental data, the second server obtains environmental data without data loss, and obtains the second environmental data. The second server determines a concentration of a sampled gas in the second environmental data, and if the concentration of the sampled gas exceeds a preset concentration threshold, the second server sends warning information to a terminal device.

Figure 2:
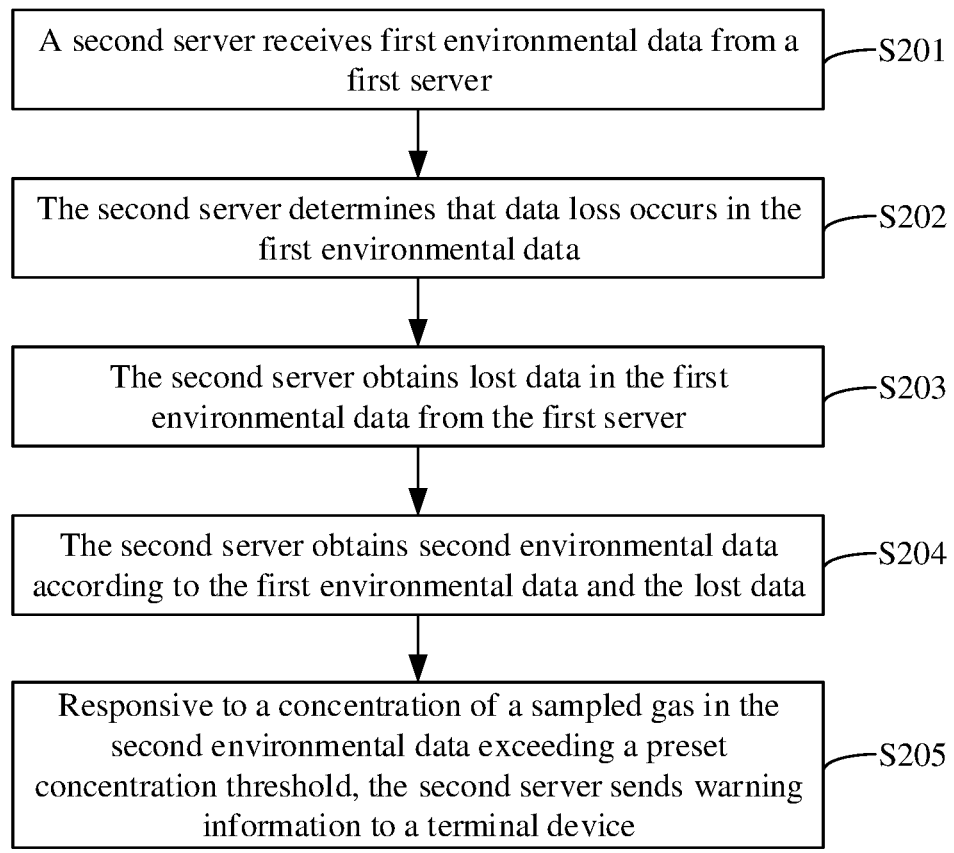
FIG. 2 is a schematic flowchart of a method for monitoring environmental data provided by one embodiment of this disclosure.

Referring to FIG. 1 and FIG. 2, this disclosure provides a method for monitoring environmental data, applied to a monitoring system. The monitoring system includes a first server and a second server. The monitoring method includes the following operations.

At S201, the second server receives first environmental data from the first server.

The first environmental data is data obtained after the first server processes the initial environmental data. The first server receives initial environmental data from a measurement device in a clean room. The initial environmental data includes concentrations of sampled gases in at least one sampling point. Each sampling point includes concentrations of multiple sampled gases. The initial environmental data is originally scattered and disordered data. The first server summarizes and organizes the initial environmental data to obtain the first environmental data. The summarization and organization are to associate the concentration of each sampled gas with the sampling point to which the sampled gas belongs. For example, the sampling point is named a sampling point A, and concentrations of multiple sampled gases obtained at the sampling point should be organized corresponding to the sampling point A to obtain a concentration of a group of sampled gases at the sampling point A. Each sampling point includes the concentrations of multiple sampled gases. It can also be said that each sampling point includes multiple sampling items. Each sampling item corresponds to one type of sampled gas. The sampled gas, or the sampling item, includes, for example, acid gas sampling, ammonia gas sampling, and the like.

In an optional embodiment, the transmission of the first environmental data is performed between the first server and the two servers through a transcription program. The transcription program is used for transcribing the first environmental data on the first server to the second server. The transcription program can be set on the first server or the second server. The transcription program transcribes data based on a row mapping instruction or a rowID mapping instruction.

At S202, the second server determines that data loss occurs in the first environmental data.

In an optional embodiment, a database is provided in the second server. Reference data used for determining whether data is lost is stored in the database. If the second server determines that the first environmental data does not match the reference data, the second server determines that data loss occurs in the first environmental data. The mismatching means that the sampling points, the sampled gases, or the sampling items included in the first environmental data does not match the sampling points, sampled gases, or sampling items in the reference data, then it is determined that data loss occurs in the first environmental data. For example, the reference data includes a sampling point A, a sampling point B, and a sampling point C. Each sampling point includes an acid gas sampling concentration, a sulfur-containing compound gas sampling concentration, and an organic gas sampling concentration. If the first environmental data includes the sampling point A and the sampling point B, it is determined that data loss occurs in the first environmental data. Alternatively, if the first environmental data includes the sampling point A, the sampling point B, and the sampling point C, and the sampling point A does not include the acid gas sampling concentration, it is determined that data loss occurs in the first environmental data.

At S203, the second server obtains lost data in the first environmental data from the first server.

After determining that data loss occurs in the first environmental data, the second server needs to obtain the lost data in the first environmental data from the first server. The lost data in the first environmental data is determined after the second server matches the first environmental data with the reference data. In an optional embodiment, the second server sends a data sending instruction to the first server. The data sending instruction is used for instructing the first server to send the lost data in the first environmental data. After receiving the data sending instruction, the first server sends the lost data in the first environmental data to the second server.

At S204, the second server obtains second environmental data according to the first environmental data and the lost data.

In this case, the second environmental data matches the reference data, and is the data that can completely reflect the conditions of airborne molecular contaminants in the clean room. Based on the explanation of the mismatching in operation S202, the matching means that after all the sampling points and the concentrations of the sampled gases included in the second environmental data are compared with all the sampling points and the concentrations of all the sampled gases included in the reference data, the sampling points included in the second environmental data match the sampling points included in the reference data, and the concentrations of the sampled gases included in the second environmental data match the concentrations of the sampled gases included in the reference data. For example, the reference data includes a sampling point A, a sampling point B, and a sampling point C. Each sampling point includes an acid gas sampling concentration, a sulfur-containing compound gas sampling concentration, and an organic gas sampling concentration. The second environmental data also includes the same sampling point A, sampling point B, and sampling point C as the reference data. Each sampling point includes an acid gas sampling concentration, a sulfur-containing compound gas sampling concentration, and an organic gas sampling concentration. Each sampling point including the acid gas sampling concentration, the sulfur-containing compound gas sampling concentration, and the organic gas sampling concentration means that each sampling point includes acid gas sampling concentration data, sulfur-containing compound gas sampling concentration data, and organic gas sampling concentration data.

At S205, responsive to a concentration of a sampled gas in the second environmental data exceeding a preset concentration threshold, the second server sends warning information to a terminal device.

Based on the example of operation S202, the second server determining whether the concentration of the sampled gas in the second environmental data exceeds a preset concentration threshold means that the second server judges the acid gas sampling concentration data, the sulfur-containing compound gas sampling concentration data, and the organic gas sampling concentration data in the second environmental data, so as to determine whether the acid gas sampling concentration exceeds a preset concentration threshold of the acid gas sampling concentration, the sulfur-containing compound gas sampling concentration exceeds a preset concentration threshold of the sulfur-containing compound gas sampling concentration, and the organic gas sampling concentration exceeds a preset concentration threshold of the organic gas sampling concentration. If the concentration of any sampled gas exceeds the preset concentration threshold, the second server sends warning information to the terminal. Both the preset concentration threshold and the reference data can be set by the staff according to actual needs, which is not limited in this disclosure.

According to the method for monitoring environmental data provided in this disclosure, after the second server determines that data loss occurs in the first environmental data, the second server obtains the lost data in the first environmental data from the first server, then obtains second environmental data according to the first environmental data and the lost data. In this case, the second environmental data is complete data that can reflect the concentrations of the sampled gases in the clean room. Therefore, the monitoring result of the clean room generated based on the complete data can also accurately reflect the conditions of the air pollutants in the clean room. Therefore, compared with the existing technology, the method for monitoring environmental data provided in this embodiment can resolve the problem of inaccurate monitoring results of airborne molecular contaminants in the clean room.

Figure 3:
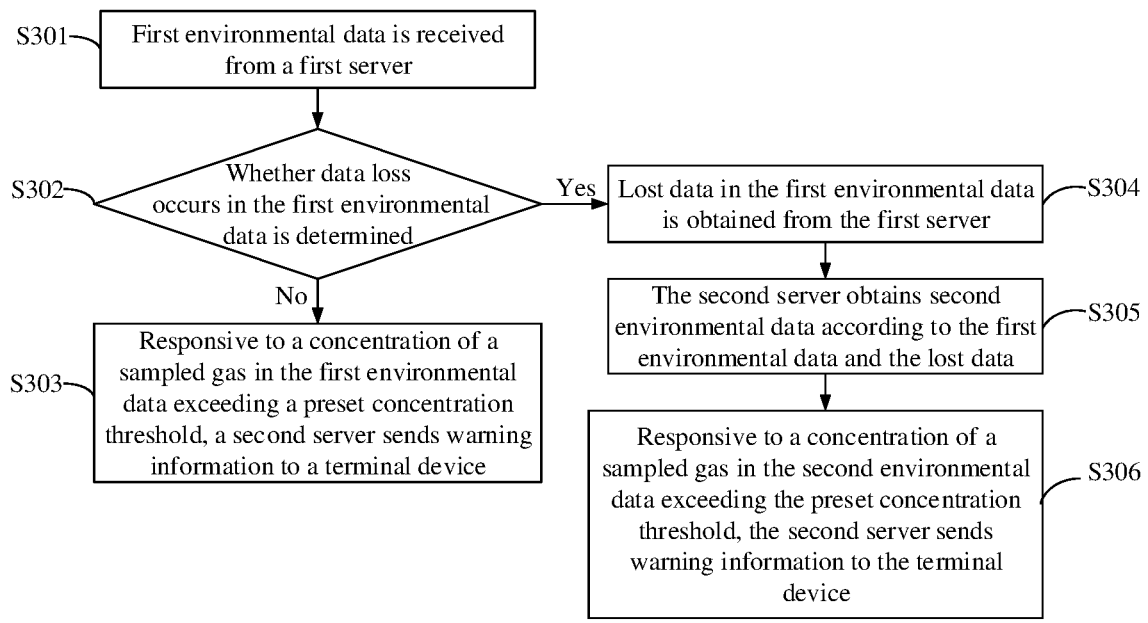
FIG. 3 is a schematic flowchart of a method for monitoring environmental data provided by another embodiment of this disclosure.

Referring to FIG. 3, in one embodiment of this disclosure, the method for monitoring environmental data includes the following operations.

At S301, the second server receives first environmental data from the first server.

Based on the explanation in operation S201, it is no longer described in detail here.

At S302, the second server determines whether data loss occurs in the first environmental data.

Based on the explanations in operation S202 and operation S204, the second server is provided with a database. After the first environmental data is compared with the reference data, if the first environmental data does not match the reference data, it is determined that data loss occurs in the first environmental data. If the first environmental data matches the reference data, it is determined that no data loss occurs in the first environmental data. If no data loss occurs in the first environmental data, operation S303 is executed, and if data loss occurs in the first environmental data, operation S304 is executed.

At S303, if a concentration of a sampled gas in the first environmental data exceeds the preset concentration threshold, the second server sends warning information to a terminal device.

If no data loss occurs in the initial environmental data sent by the first server to the second server during the transmission, or no data loss occurs in the first environmental data, the second server determines whether the concentration of the sampled gas in the first environmental data exceeds the preset concentration threshold. In this case, the data on which the second server performs environmental data monitoring is the collected complete environmental data of the clean room. Therefore, the obtained monitoring results can also truly and accurately reflect the concentration conditions of airborne molecular contaminants in the clean room. Based on the explanation of operation S205, the second server determining whether the concentration of the sampled gas in the first environmental data exceeds a preset concentration threshold means that the acid gas sampling concentration data, the sulfur-containing compound gas sampling concentration data, and the organic gas sampling concentration data in the first environmental data are determined, so as to determine whether the acid gas sampling concentration exceeds a preset concentration threshold of the acid gas sampling concentration, the sulfur-containing compound gas sampling concentration exceeds a preset concentration threshold of the sulfur-containing compound gas sampling concentration, and the organic gas sampling concentration exceeds a preset concentration threshold of the organic gas sampling concentration. If the concentration of any sampled gas exceeds the preset concentration threshold, the second server sends warning information to the terminal. Both the preset concentration threshold and the reference data can be set by the staff according to actual needs, which is not limited in this disclosure.

At S304, the second server obtains lost data in the first environmental data from the first server.

Based on the explanation of operation S203, if data loss occurs in the first environmental data, the second server needs to obtain the lost data in the first environmental data from the first server. The lost data in the first environmental data is determined after the second server matches the first environmental data with the reference data.

At S305, the second server obtains second environmental data according to the first environmental data and the lost data.

In this case, the second environmental data is the data that can completely reflect the conditions of airborne molecular contaminants in the clean room. The results determined after the second server determines the concentration of the sampled gas in the second environmental data are also accurate monitoring results for the conditions of the airborne molecular contaminants in the clean room.

At S306, if a concentration of a sampled gas in the second environmental data exceeds the preset concentration threshold, the second server sends warning information to a terminal device.

Specifically, the second server determines whether the concentration of the sampled gas in the second environmental data exceeds the preset concentration threshold, and if the concentration of the sampled gas in the second environmental data exceeds the preset concentration threshold, the second server sends warning information to a terminal device. Based on the explanation of operation S205, the second server determining whether the concentration of the sampled gas in the second environmental data exceeds a preset concentration threshold means that the acid gas sampling concentration data, the sulfur-containing compound gas sampling concentration data, and the organic gas sampling concentration data in the second environmental data are determined, so as to determine whether the acid gas sampling concentration exceeds a preset concentration threshold of the acid gas sampling concentration, the sulfur-containing compound gas sampling concentration exceeds a preset concentration threshold of the sulfur-containing compound gas sampling concentration, and the organic gas sampling concentration exceeds a preset concentration threshold of the organic gas sampling concentration. If the concentration of any sampled gas exceeds the preset concentration threshold, the second server sends warning information to the terminal. Both the preset concentration threshold and the reference data can be set by the staff according to actual needs, which is not limited in this disclosure.

According to the method for monitoring environmental data provided in this disclosure, after the second server receives the first environmental data from the first server, the second server determines whether data loss occurs in the first environmental data. If no data loss occurs in the first environmental data, the second server determines whether the concentration of the sampled gas in the first environmental data exceeds the preset concentration threshold; and if the concentration of the sampled gas in the first environmental data exceeds the preset concentration threshold, the second server sends warning information to the terminal device. If data loss occurs in the first environmental data, the second server obtains the lost data from the first server; and the second server obtains the second environmental data according to the first environmental data and the lost data, and determines, according to the second environmental data, whether to send warning information to a terminal device. The second server determines whether a concentration of a sampled gas in a clean room exceeds a preset concentration threshold based on complete data of the concentrations of the sampled gases in the clean room. Therefore, monitoring results of the clean room generated based on the complete data can also accurately reflect the conditions of air pollutants in the clean room. Therefore, compared with the existing technology, the method for monitoring environmental data provided in this embodiment can resolve the problem of inaccurate monitoring results of airborne molecular contaminants in the clean room.

Figure 4:
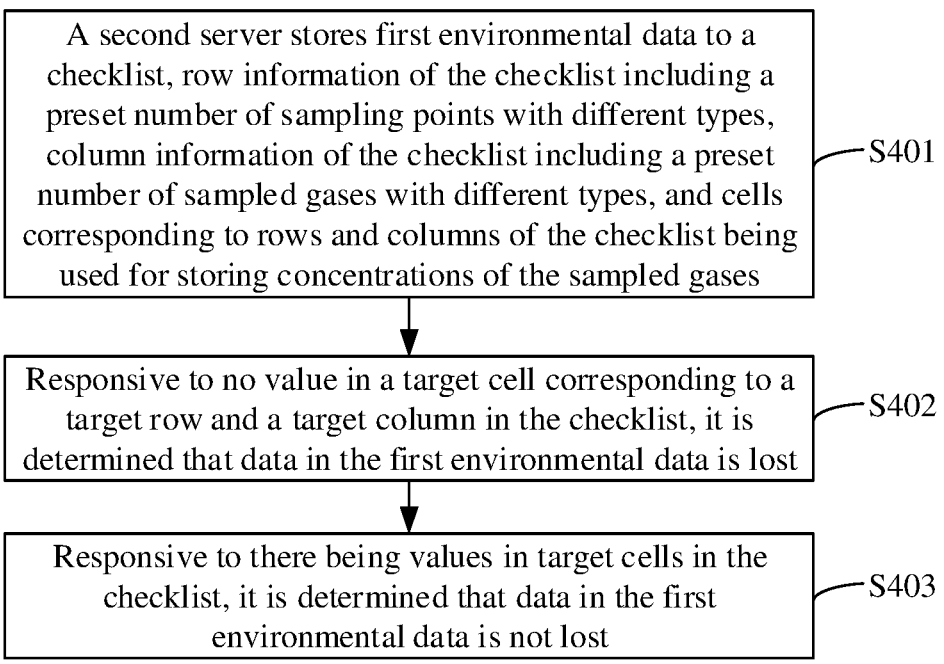
FIG. 4 is a schematic flowchart of a method for monitoring environmental data provided by yet another embodiment of this disclosure.

On the basis of the embodiment as shown in FIG. 3, in one embodiment of this disclosure, the second server can determine that data loss occurs in the first environmental data through operations as shown in FIG. 4. That is, operation S202 may include the following operations.

At S401, the second server stores the first environmental data to a checklist. Row information of the checklist includes a preset number of sampling points with different types. Column information of the checklist includes a preset number of sampled gases with different types. Cells corresponding to rows and columns of the checklist are used for storing concentrations of the sampled gases.

The checklist can also be referred to as a Tag list. The row information of the checklist includes a preset number of sampling points with different types. The column information of the checklist includes a preset number of sampled gases with different types. However, if data loss occurs in the first environmental data, during the first environmental data is stored in the checklist, the preset number of sampling points with different types cannot be filled completely, and/or the preset number of gases with different types cannot be filled, which may cause that the cells in the checklist cannot be filled.

At S402, responsive to no value in a target cell corresponding to a target row and a target column in the checklist, it is determined that data in the first environmental data is lost.

The target row may be all rows corresponding to the preset number of sampling points with different types, or may be rows corresponding to part of the preset number of sampling points with different types. The target column may be all rows corresponding to the preset number of sampled gases with different types, or may be rows corresponding to part of the preset number of sampled gases with different types. The target row and the target column in the checklist can be set by the staff according to actual needs. Responsive to no value in the target cell, it can be determined that the data in the first environmental data is lost. In an optional embodiment, the second server stores a reference list generated according to the reference data. Row information of the reference list includes the preset number of sampling points with different types. Column information of the reference list includes the preset number of sampled gases with different types. The cells corresponding to the rows and columns of the reference list are used for storing the preset concentration of the sampled gases. Upon comparison of the checklist with the reference list, it can also be determined whether data loss occurs in the first environmental data.

Specifically, the cell(s) storing the value(s) in the reference list is the target cell(s). If there is no value in the target cell(s) in the checklist, it is determined that the data in the first environmental data is lost.

At S403, responsive to there being value in a target cell in the checklist, it is determined that data in the first environmental data is not lost.

In this case, the second server can determine whether the concentration of the sampled gas in the first environmental data exceeds a preset concentration. The concentration of the sampled gas is the value in the target cell. The target cell corresponds to different types of sampled gases. For example, the row corresponding to the first target cell is the sampling point A, and the column corresponding to the target cell is acid gas sampling, then the second server determines whether the value in the first target cell exceeds the preset concentration threshold, if the value exceeds the preset concentration threshold, the second server sends warning information to the terminal device.

In an optional embodiment, the value in the target cell in the reference list may be the preset concentration threshold, and the second server can compare the values in the target cells in the checklist based on the reference list, so as to determine whether the values in the target cells in the checklist exceed various preset concentration thresholds of the target cells corresponding to the reference list. If the values exceed the preset concentration thresholds, the second server sends the warning information to the terminal device.

The checklist can also be replaced with other data representation forms, as long as it can indicate the gas concentration corresponding to different types of sampling points and different types of sampled gases.

In one embodiment of this disclosure, before operation S202, the method for monitoring environmental data further includes the following operations.

The second server receives a data comparison instruction from the first server. The data comparison instruction is used for instructing the second server to determine whether data loss occurs in the first environmental data.

Figure 5:
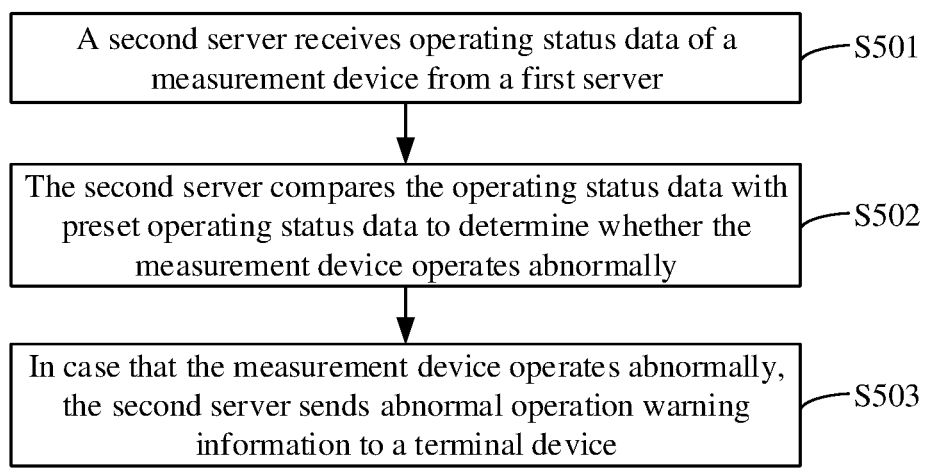
FIG. 5 is a schematic flowchart of a method for monitoring environmental data provided by still another embodiment of this disclosure.

After the first server sends the first environmental data to the second server, a data comparison instruction is generated. After the second server receives the data comparison instruction, the second server determines whether data loss occurs in the first environmental data. If data loss occurs in the first environmental data, the second server may obtain the lost data in the first environmental data from the first server.

referring to FIG. 5, an embodiment of the present application also provides a method for monitoring operating status of a measurement device. The method of this embodiment can run independently, or can run on the basis of the embodiments shown in FIG. 2, FIG. 3, and FIG. 4. The method for monitoring operating status of a measurement device includes the following operations.

At S501, the second server receives operating status data of a measurement device from the first server.

The operating status data of the measurement device may include a nitrogen pressure used by the measurement device, the operating temperature of a pump of the measurement device, etc. An analysis system of the measurement device may send the operating status data to the first server, and then the first server sends the operating status data to the second server.

At S502, the second server compares the operating status data with preset operating status data to determine whether the measurement device operates abnormally.

The preset operating status data is stored in the second server. The second server can compare the operating status data with the preset operating status data to determine whether the measurement device operates abnormally. For example, the temperature range of the pump of the measurement device in the preset operating status data is 25° C.-50° C., and the temperature of the pump of the measurement device in the operating status data is 70° C., then it is determined that the measurement device operates abnormally.

At S503, in case that the measurement device operates abnormally, the second server sends abnormal operation warning information to the terminal device.

After receiving the abnormal operation warning information through the terminal device, the staff can immediately take measures. For example, the measurement device is calibrated to solve the abnormal operating status of the measurement device, to avoid damage to the measurement device.

The method for monitoring operating status of a measurement device provided in this embodiment can monitor the operating status of the measurement device. When the measurement device operates abnormally, the staff may be notified in time to prevent damage to the measurement device. The method for monitoring operating status of a measurement device provided in this embodiment can also assist the staff in analyzing the operating status of the measurement device in a certain period of time, so as to achieve the effect of early warning of the failure of the measurement device.

Figure 6:
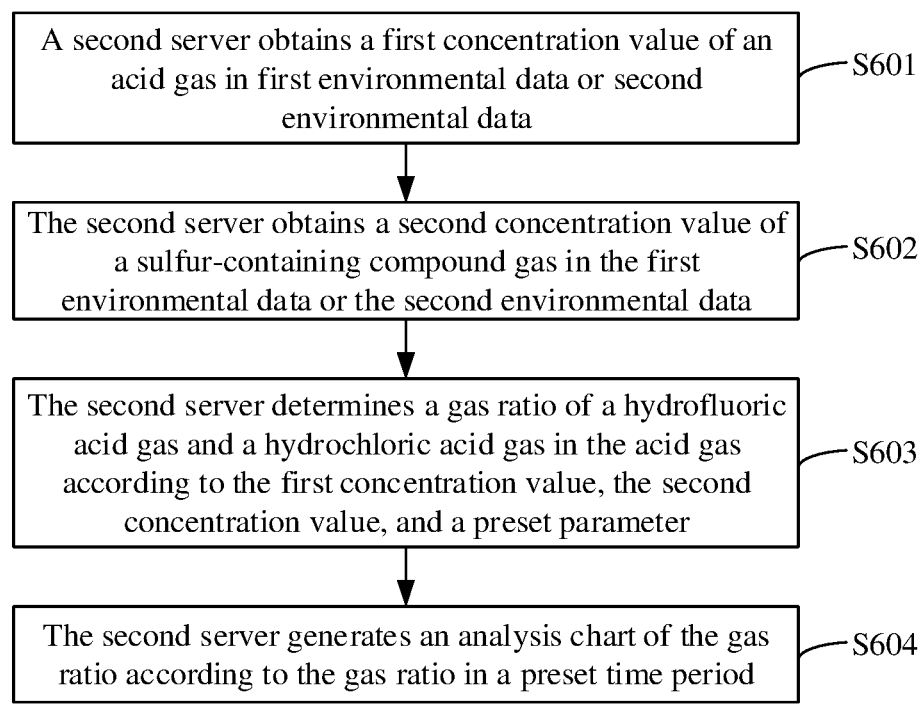
FIG. 6 is a schematic flowchart of a method for monitoring environmental data provided by further another embodiment of this disclosure.

Referring to FIG. 6, in one embodiment of this disclosure, after operation S202 or operation S302, the following operations are further executed.

At S601, the second server obtains a first concentration value of an acid gas in the second environmental data.

The acid gas includes a hydrofluoric acid gas, a hydrochloric acid gas, a sulfur dioxide gas, etc. The first concentration value represents a concentration value of the acid gas. The first concentration value is sent by the measurement device to the first server, and then sent by the first server to the second server. If no data loss occurs in the first environmental data, the second server obtains the first concentration value of the acid gas in the first environmental data.

At S602, the second server obtains a second concentration value of a sulfur-containing compound gas in the second environmental data.

The sulfur-containing compound gas may include sulfur dioxide gas, sulfur trioxide gas, and the like. The second concentration value is sent by the measurement device to the first server, and then sent by the first server to the second server. If no data loss occurs in the first environmental data, the second server obtains the second concentration value of the sulfur-containing compound gas in the first environmental data.

At operation 603, the second server determines a gas ratio of a hydrofluoric acid gas and a hydrochloric acid gas in the acid gas according to the first concentration value, the second concentration value, and a preset parameter.

The parameter $$T(F^-, Cl^-) = 1 - \frac{TS}{TA}$$

is defined in the second server, where T represents the gas ratio of the hydrofluoric acid gas and the hydrochloric acid gas in the acid gas, TA represents the first concentration value, and TS represents the second concentration value.

At operation 604, the second server generates an analysis chart of the gas ratio according to the gas ratio in a preset time period.

Figure 7:
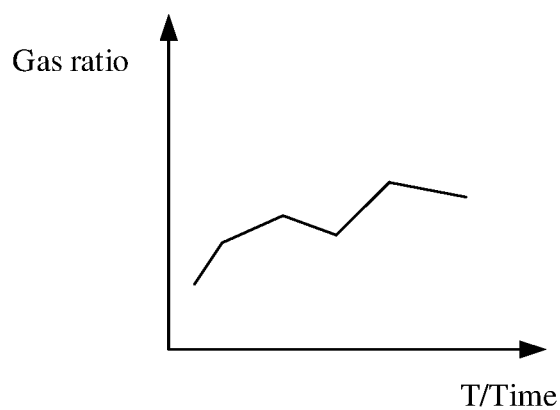
FIG. 7 is a schematic flowchart of an analysis chart provided by one embodiment of this disclosure.

As shown in FIG. 7, the abscissa of the analysis chart is time, and the ordinate of the analysis chart is the gas ratio. Through the analysis chart, the staff can more intuitively obtain the change in the gas ratio of the hydrofluoric acid gas and the hydrochloric acid gas in the acid gas.

In one embodiment of this disclosure, if no data loss occurs in the first environmental data, the second server may also summarize and organize the first environmental data collected at different moments, and analyze the first environmental data. In this way, the change trend of the air pollution conditions of the clean room is known, so as to early warn the air pollution of the clean room. If data loss occurs in the first environmental data, the second server summarizes and organizes the second environmental data collected at different moments, and analyzes the second environmental data. In this way, the change trend of the air pollution conditions of the clean room is known, so as to early warn the air pollution of the clean room.

Figure 8:
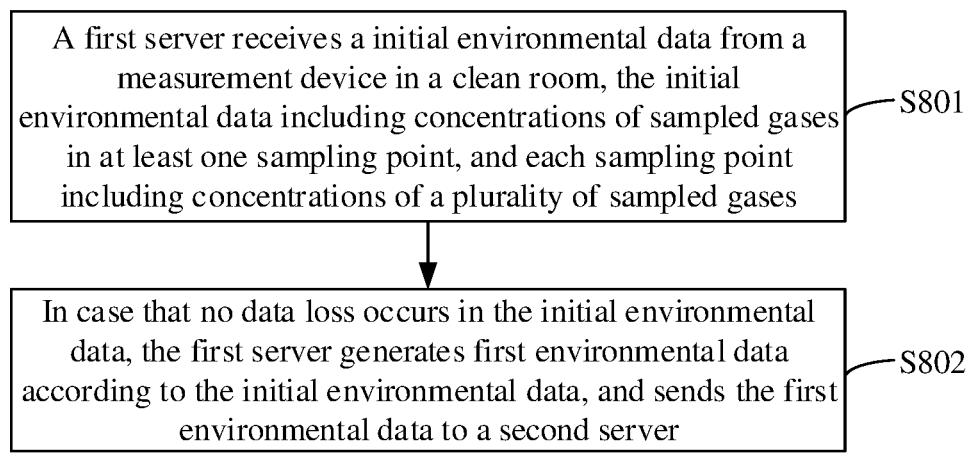
FIG. 8 is a schematic flowchart of a method for monitoring environmental data provided by further another embodiment of this disclosure.

Referring to FIG. 8, the method for monitoring environmental data is described in the embodiment as shown in FIG. 8 from the perspective of the first server. The monitoring method includes the following operations.

At S801, the first server receives initial environmental data from a measurement device in a clean room. The initial environmental data includes concentrations of sampled gases in at least one sampling point. Each sampling point includes concentrations of multiple sampled gases.

Before obtaining the initial environmental data, the measurement device obtains pulse signals collected at different sampling points. The measurement device can convert the pulse signals into data and send the data to the first server. The initial environmental data includes the concentrations of the sampled gases in at least one sampling point. Each sampling point includes the concentrations of multiple sampled gases. If the initial environmental data is not lost, the sampling points included in the initial environmental data are a preset number of sampling points with different types stored in the second server, and the sampled gases included in the initial environmental data are a preset number of sampled gases with different types stored in the second server.

At S802, if no data loss occurs in the initial environmental data, the first server generates first environmental data according to the initial environmental data, and sends the first environmental data to the second server.

The initial environmental data is originally scattered and disordered data. The first server summarizes and organizes the initial environmental data to obtain the first environmental data. The summarization and organization are to associate the concentration of each sampled gas with the sampling point to which the sampled gas belongs. For example, the sampling point is named a sampling point A, and concentrations of multiple sampled gases obtained at the sampling point should be organized corresponding to the sampling point A to obtain a concentration of a group of sampled gases at the sampling point A. Each sampling point includes the concentrations of multiple sampled gases. It can also be said that each sampling point includes multiple sampling items. Each sampling item corresponds to one type of sampled gas. The sampled gas, or the sampling item, includes, for example, acid gas sampling, ammonia gas sampling, and the like. In an optional embodiment, the first server is provided with data processing software. The data processing software (such as CRIO) can convert the pulse signal sent by the measurement device into data, and then another data processing software (such as PC-Client) reorganizes the data, that is, summarizes and organizes the initial environmental data to obtain the first environmental data. The summarization and organization are to associate the concentration of each sampled gas with the sampling point to which the sampled gas belongs.

In this embodiment, the first server can determine whether data loss occurs in the initial environmental data in the following manner. When the sampling points included in the initial environmental data do not match the preset sampling points, it is determined that data loss occurs in the initial environmental data. Alternatively, when the sampled gases included in the initial environmental data do not match the preset sampled gases, it is determined that data loss occurs in the initial environmental data.

Specifically, if the initial environmental data is not lost, the sampling points included in the initial environmental data should match the preset sampling points, that is, should match the preset number of sampling points with different types stored in the second server. If the sampling points included in the initial environmental data do not match the preset sampling points, it is determined that data loss occurs in the initial environmental data. If the initial environmental data is not lost, the sampled gases included in the initial environmental data should match the preset sampled gases, that is, match the preset number of sampled gases with different types stored in the second server. If the sampled gases included in the initial environmental data do not match the preset sampled gases, it is determined that data loss occurs in the initial environmental data. As long as it is determined that the sampling points included in the initial environmental data do not match the preset sampling points, or it is determined that the sampled gases included in the initial environmental data do not match the preset sampled gases, it can be determined that data loss occurs in the initial environmental data.

In an optional embodiment, after operation S802, the first environmental data is stored in the first server. After the first server generates the first environmental data according to the initial environmental data, the first environmental data can be stored, and the staff can view the first environmental data later to evaluate the working performance of the first server, etc., thereby improving the data loss situation of the environmental data in the transmission process.

In the method for monitoring environmental data provided in this embodiment, when receiving the initial environmental data, the first server makes a judgment on whether data loss occurs in the initial environmental data. When data loss occurs in the initial environmental data, the first server obtains the initial environmental data again from the measurement device, or obtains the lost data in the initial environmental data from the measurement device, and integrates the initial environmental data and the lost data in the initial environmental data to generate the first environmental data, and sends the first environmental data to the second server. Because the first server first determines whether the data uploaded by the measurement device is lost, and if the data uploaded by the measurement device is lost, the data uploaded by the measurement device is obtained again, to ensure the integrity of the first environmental data. In combination with the second server determining the integrity of the first environmental data, the method for monitoring environmental data provided in this embodiment can perform multiple integrity checks on the environmental data in the transmission process to prevent the environmental data from losing in the transmission process, affecting the monitoring of airborne molecular contaminants in the clean room.

Figure 9:
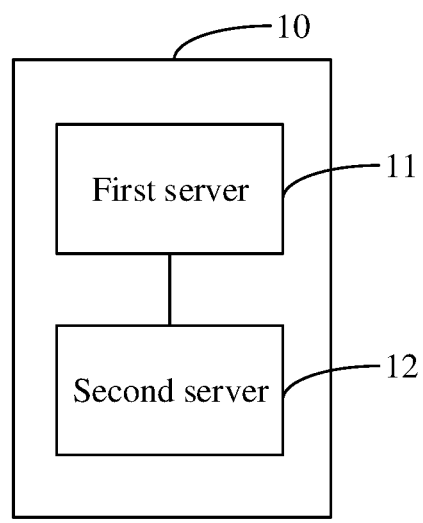
FIG. 9 is a schematic diagram of a monitoring system provided by one embodiment of this disclosure.

Referring to FIG. 9, this disclosure further provides a monitoring system 10, including a first server 11 and a second server 12.

The first server 11 is configured to: receive initial environmental data from a measurement device in a clean room, the initial environmental data including concentrations of sampled gases in at least one sampling point, and each sampling point including concentrations of multiple sampled gases; if no data loss occurs in the initial environmental data, generate first environmental data according to the initial environmental data, and send the first environmental data to a second server.

The second server 12 is configured to: receive the first environmental data from the first server; determine that data loss occurs in the first environmental data; obtain lost data in the first environmental data from the first server; obtain second environmental data according to the first environmental data and the lost data; and responsive to a concentration of a sampled gas in the second environmental data exceeding a preset concentration threshold, send warning information to a terminal device.

The second server is further configured to: receive first environmental data from a first server, and determine whether data loss occurs in the first environmental data; if no data loss occurs in the first environmental data, determine whether the concentration of the sampled gas in the first environmental data exceeds a preset concentration threshold, and if the concentration of the sampled gas in the first environmental data exceeds the preset concentration threshold, send warning information to a terminal device; if data loss occurs in the first environmental data, obtain the lost data in the first environmental data from the first server, obtain second environmental data according to the first environmental data and the lost data, determine whether the concentration of the sampled gas in the second environmental data exceeds a preset concentration threshold, and if the concentration exceeds the preset concentration threshold, send warning information to the terminal device.

The first server 11 is further configured to determine that data loss occurs in the initial environmental data when the sampling points included in the initial environmental data do not match the preset sampling points, or determine that data loss occurs in the initial environmental data when the sampled gases included in the initial environmental data do not match the preset sampled gases.

The first server 11 is further configured to store the first environmental data.

The second server 12 is specifically configured to: store the first environmental data to a checklist, row information of the checklist including a preset number of sampling points with different types, column information of the checklist including a preset number of sampled gases with different types, and cells corresponding to rows and columns of the checklist being used for storing concentrations of the sampled gases; and responsive to no value in a target cell corresponding to a target row and a target column in the checklist, determine that data in the first environmental data is lost.

The second server 12 is further configured to receive a data comparison instruction from the first server. The data comparison instruction is used for instructing the second server to determine whether data loss occurs in the first environmental data.

The second server 12 is further configured to: receive operating status data of a measurement device from the first server, compare the operating status data with preset operating status data to determine whether the measurement device operates abnormally, and in case that the measurement device operates abnormally, send abnormal operation warning information to the terminal device.

The second server 12 is further configured to: obtain a first concentration value of an acid gas in the second environmental data; obtain a second concentration value of a sulfur-containing compound gas in the second environmental data; determine a gas ratio of a hydrofluoric acid gas and a hydrochloric acid gas in the acid gas according to the first concentration value, the second concentration value, and a preset parameter; and generate an analysis chart of the gas ratio according to the gas ratio in a preset time period.

Figure 10:
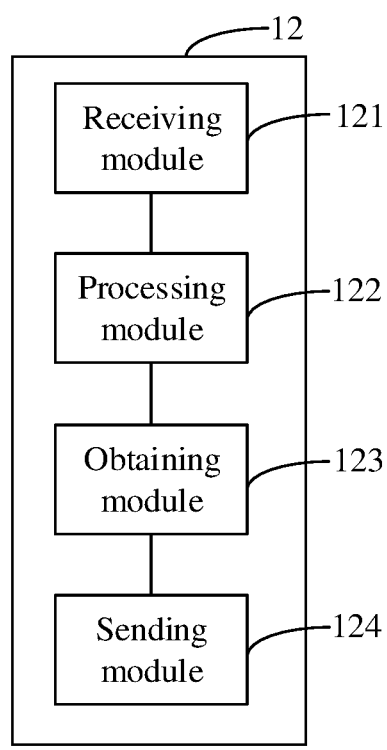
FIG. 10 is a schematic diagram of a second server provided by one embodiment of this disclosure.

Referring to FIG. 10, this disclosure further provides a second server 12. The second server 12 includes a receiving module 121, a processing module 122, an obtaining module 123, and a sending module 124.

The receiving module 121 is configured to receive first environmental data from the first server.

The processing module 122 is configured to determine that data loss occurs in the first environmental data.

The obtaining module 123 is configured to obtain lost data in the first environmental data from the first server.

The processing module 122 is configured to obtain second environmental data according to the first environmental data and the lost data.

The sending module 124 is configured to send warning information to the terminal device responsive to a concentration of a sampled gas in the second environmental data exceeding a preset concentration threshold.

In an optional embodiment, the second server 12 further includes a storage module, configured to store the first environmental data to a checklist. Row information of the checklist includes a preset number of sampling points with different types. Column information of the checklist includes a preset number of sampled gases with different types. Cells corresponding to rows and columns of the checklist are used for storing concentrations of the sampled gases.

The processing module 122 is further configured to determine that data in the first environmental data is lost responsive to no value in a target cell corresponding to a target row and a target column in the checklist.

The receiving module 121 is further configured to receive a data comparison instruction from the first server. The data comparison instruction is used for instructing the second server to determine whether data loss occurs in the first environmental data.

The receiving module 121 is further configured to receive operating status data of a measurement device from the first server.

The processing module 122 is further configured to compare the operating status data with preset operating status data to determine whether the measurement device operates abnormally.

The sending module 124 is further configured to send abnormal operation warning information to the terminal device in case that the measurement device operates abnormally.

The obtaining module 123 is further configured to obtain a first concentration value of an acid gas in the second environmental data, and obtain a second concentration value of a sulfur-containing compound gas in the second environmental data.

In an optional embodiment, the second server 12 further includes a processing module, configured to determine a gas ratio of a hydrofluoric acid gas and a hydrochloric acid gas in the acid gas according to the first concentration value, the second concentration value, and a preset parameter, and to generate an analysis chart of the gas ratio according to the gas ratio in a preset time period.

Figure 11:
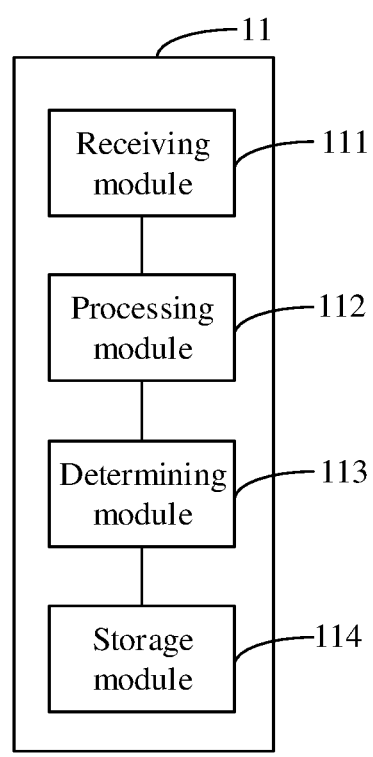
FIG. 11 is a schematic diagram of a first server provided by one embodiment of this disclosure.

Referring to FIG. 11, this disclosure further provides a first server 11. The first server 11 includes a receiving module 111 and a processing module 112.

The receiving module 111 is configured to receive initial environmental data from a measurement device in a clean room. The initial environmental data includes concentrations of sampled gases in at least one sampling point. Each sampling point includes concentrations of multiple sampled gases.

The processing module 112 is configured to: generate first environmental data according to the initial environmental data in case that no data loss occurs in the initial environmental data, and send the first environmental data to the second server.

In an optional embodiment, the first server further includes a determining module and a storage module. The determining module is configured to: determine that data loss occurs in the initial environmental data in case that the sampling points included in the initial environmental data do not match the preset sampling points, or determine that data loss occurs in the initial environmental data in case that the sampled gases included in the initial environmental data do not match the preset sampled gases. The storage module is configured to store the first environmental data.

It should be noted that the terms "including", "comprising" or any other variants thereof herein are intended to cover non-exclusive inclusion, so that a process, method, article or apparatus including a series of elements not only includes those elements, but also includes other elements that are not explicitly listed, or elements inherent to the process, method, article or apparatus. Without more restrictions, the element defined by the sentence "including a . . . " does not exclude the existence of other identical elements in the process, method, article or apparatus including the element.

The sequence numbers of the embodiments of this disclosure are merely for description but do not imply the preference among the embodiments.

Through the description of the above implementations, those skilled in the art can clearly understand that the method of the above embodiments can be implemented by means of software and the necessary general hardware platform, and certainly can also be implemented by hardware. However, in many cases, the former is better. Based on such an understanding, the technical solution of this disclosure essentially or the part that contributes to the existing technology can be embodied in the form of a software product, and the computer software product is stored in a storage medium (such as an ROM/RAM, a magnetic disk, an optical disk), including several instructions that cause a terminal device (which can be a mobile phone, a computer, a server, an air conditioner, or a network device, etc.) to execute the method described in each embodiment of this disclosure.

This disclosure is described with reference to flowcharts and/or block diagrams of methods, devices (systems), and computer program products according to embodiments of this disclosure. It should be understood that each process and/or block in the flowchart and/or block diagram, and the combination of the processes and/or blocks in the flowchart and/or block diagram can be implemented by computer program instructions. These computer program instructions can be provided to a processor of a general-purpose computer, a special-purpose computer, an embedded processor, or other programmable data processing devices to generate a machine, so that the instructions executed by the processor of the computer or other programmable data processing devices generate an apparatus for implementing the functions specified in one or more processes in the flowchart and/or one or more blocks in the block diagram.

These computer program instructions can also be stored in a computer readable memory that can direct a computer or other programmable data processing devices to work in a specific manner, so that the instructions stored in the computer readable memory produce an article of manufacture including an instruction apparatus. The instruction apparatus implements the functions specified in one or more processes in the flowchart and/or one or more blocks in the block diagram.

These computer program instructions can also be loaded on a computer or other programmable data processing devices, so that a series of operation steps are executed on the computer or other programmable devices to produce computer-implemented processing, and thus, the instructions executed on the computer or other programmable devices provide steps for implementing the functions specified in one or more processes in the flowchart and/or one or more blocks in the block diagram.

The above are only preferred embodiments of this disclosure, and do not limit the scope of this application. Any equivalent structure or equivalent process transformation made using the content of the specification and drawings of this application, or directly or indirectly used in other related technical field falls within the scope of patent protection of this application.

The invention claimed is:

1. A method for monitoring environmental data, applied to a monitoring system comprising a first server and a second server, the method comprising:
   receiving, by the second server, first environmental data from the first server;
   determining, by the second server, that data loss occurs in the first environmental data;
   obtaining, by the second server, lost data in the first environmental data from the first server;
   obtaining, by the second server, second environmental data according to the first environmental data and the lost data; and
   responsive to a concentration of a sampled gas in the second environmental data exceeding a preset concentration threshold, sending, by the second server, warning information to a terminal device.

2. The method of claim 1, wherein the determining, by the second server, that the data loss occurs in the first environmental data comprises:
   storing, by the second server, the first environmental data to a checklist, row information of the checklist comprising a preset number of sampling points with different types, column information of the checklist comprising a preset number of sampled gases with different types, and cells corresponding to rows and columns of the checklist being used for storing concentrations of the sampled gases; and
   responsive to no value in a target cell corresponding to a target row and a target column in the checklist, determining that data in the first environmental data is lost.

3. The method of claim 2, wherein before the determining, by the second server, that the data loss occurs in the first environmental data, the method further comprises:
receiving, by the second server, a data comparison instruction from the first server, the data comparison instruction being used for instructing the second server to determine whether the data loss occurs in the first environmental data.

4. The method of claim 2, further comprising:
receiving, by the second server, operating status data of a measurement device from the first server;
comparing, by the second server, the operating status data with preset operating status data to determine whether the measurement device operates abnormally; and
in case that the measurement device operates abnormally, sending, by the second server, abnormal operation warning information to the terminal device.

5. The method of claim 2, further comprising:
obtaining, by the second server, a first concentration value of an acid gas in the second environmental data;
obtaining, by the second server, a second concentration value of a sulfur-containing compound gas in the second environmental data;
determining, by the second server, a gas ratio of a hydrofluoric acid gas and a hydrochloric acid gas in the acid gas according to the first concentration value, the second concentration value, and a preset parameter; and
generating, by the second server, an analysis chart of the gas ratio according to the gas ratio in a preset time period.

6. The method of claim 1, wherein before the determining, by the second server, that the data loss occurs in the first environmental data, the method further comprises:
receiving, by the second server, a data comparison instruction from the first server, the data comparison instruction being used for instructing the second server to determine whether the data loss occurs in the first environmental data.

7. The method of claim 1, further comprising:
receiving, by the second server, operating status data of a measurement device from the first server;
comparing, by the second server, the operating status data with preset operating status data to determine whether the measurement device operates abnormally; and
in case that the measurement device operates abnormally, sending, by the second server, abnormal operation warning information to the terminal device.

8. The method of claim 1, further comprising:
obtaining, by the second server, a first concentration value of an acid gas in the second environmental data;
obtaining, by the second server, a second concentration value of a sulfur-containing compound gas in the second environmental data;
determining, by the second server, a gas ratio of a hydrofluoric acid gas and a hydrochloric acid gas in the acid gas according to the first concentration value, the second concentration value, and a preset parameter; and
generating, by the second server, an analysis chart of the gas ratio according to the gas ratio in a preset time period.

9. The method of claim 1, wherein the receiving, by the second server, the first environmental data from the first server comprises:
in case that the first server receives initial environmental data from a measurement device in a clean room and no data loss occurs in the initial environmental data, the initial environmental data comprising concentrations of sampled gases in at least one sampling point, and each sampling point of the at least one sampling point comprising concentrations of a plurality of sampled gases, receiving, by the second server, the first environmental data generated by the first server according to the initial environmental data and sent by the first server.

10. The method of claim 9, wherein
responsive to a sampling point of the at least one sampling point comprised in the initial environmental data not matching a preset sampling point, determining, by the first server, that data loss occurs in the initial environmental data; or
responsive to the sampled gases comprised in the initial environmental data not matching preset sampled gases, determining, by the first server, that data loss occurs in the initial environmental data.

11. The method of claim 10, wherein after the first server generates the first environmental data according to the initial environmental data, storing, by the first server, the first environmental data.

12. The method of claim 9, wherein after the first server generates the first environmental data according to the initial environmental data, storing, by the first server, the first environmental data.

13. A monitoring system, comprising:
the first server, configured to receive initial environmental data from a measurement device in a clean room, the initial environmental data comprising concentrations of sampled gases in at least one sampling point, and each sampling point of the at least one sampling point comprising concentrations of a plurality of sampled gases, and in case that no data loss occurs in the initial environmental data, generate the first environmental data according to the initial environmental data, and send the first environmental data to the second server; and
the second server, configured to perform the method according to claim 1.

14. The monitoring system of claim 13, wherein the second server is specifically configured to:
store the first environmental data to a checklist, row information of the checklist comprising a preset number of sampling points with different types, column information of the checklist comprising a preset number of sampled gases with different types, and cells corresponding to rows and columns of the checklist being used for storing concentrations of the sampled gases; and
responsive to no value in a target cell corresponding to a target row and a target column in the checklist, determine that data in the first environmental data is lost.

* * * * *